United States Patent
Wu et al.

(10) Patent No.: US 11,008,288 B1
(45) Date of Patent: May 18, 2021

(54) METHODS FOR PREPARATION OF APREMILAST

(71) Applicant: National Taiwan Normal University, Taipei (TW)

(72) Inventors: Hsyueh-Liang Wu, Taipei (TW); Ping Yu Wu, Zhubei (TW); Jin-Fong Syu, New Taipei (TW); Julian P. Henschke, Uraidla (AU)

(73) Assignee: NATIONAL TAIWAN NORMAL UNIVERSITY, Taipei (TW)

( * ) Notice: Subject to any disclaimer, the term of this patent is extended or adjusted under 35 U.S.C. 154(b) by 0 days.

(21) Appl. No.: 16/801,697

(22) Filed: Feb. 26, 2020

(30) Foreign Application Priority Data

Dec. 30, 2019 (TW) ................................. 108148453

(51) Int. Cl.
*C07D 209/48* (2006.01)

(52) U.S. Cl.
CPC .................. *C07D 209/48* (2013.01)

(58) Field of Classification Search
CPC .................................................. C07D 209/48
See application file for complete search history.

(56) References Cited

U.S. PATENT DOCUMENTS 7,427,638 B2   9/2008   Muller et al.

OTHER PUBLICATIONS

Syu et al. "Asymmetric Synthesis of β Aryl β-Imido Sulfones Using Rhodium Catalysts with Chiral Diene Ligands: Synthesis of Apremilast" Organic Letters, 2019, vol. 21, No. 12, pp. 4614-4618.*
Tokunaga et al., "$C_2$-Symmetric Bicyclo[2.2.2]octadienes as Chiral Ligands: Their High Performance in Rhodium-Catalyzed Asymmetric Arylation of N-Tosylaylimines," J. Am. Chem. Soc. 2004, 126, 42, pp. 13584-13585, 2 pages.

* cited by examiner

*Primary Examiner* — Joseph R Kosack
(74) *Attorney, Agent, or Firm* — Muncy, Geissler, Olds and Lowe, P.C.

(57) ABSTRACT

The present invention discloses a method for preparation of Apremilast. β-phthalimino vinylsulfones are reacted through the asymmetric addition reaction to form an addition product, and the drug of Apremilast can be obtained from the addition product through simple reactions. The method is a process for synthesizing Apremilast in a more efficient way.

26 Claims, 2 Drawing Sheets

METHODS FOR PREPARATION OF APREMILAST

This application claims priority for Taiwan patent application no. 108148453 filed on Dec. 30, 2019, the content of which is incorporated by reference in its entirely.

BACKGROUND OF THE INVENTION

Technical Field

The present invention relates to a method for preparation of Apremilast.

Related Art

Apremilast (brand name: Otezla) is the first oral selective phosphodiesterase 4 (PDE4) inhibitor. The medication is the first oral drug approved for the treatment of psoriasis in last twenty years, and for the treatment of psoriatic arthritis in last fifteen years. Apremilast have been demonstrated that can enable patients to achieve clinically significant and lasting improvements in related clinical trials, and will provide a valuable treatment choice to a broad group of patients who suffer from psoriasis, including those who are treated with biological preparations or conventional systemic drugs.

U.S. Pat. No. 7,427,638 has disclosed a two-fragment synthesis of Apremilast. First, the 1-OH and 2-OH groups of the protocatechuic acid ethyl ester 102 were conjugated with a methyl and an ethyl groups, respectively (yield: 36% and 81%, respectively). The ester group of the compound 104 was then reduced to an alcohol and oxidize to an aldehyde by manganese dioxide to produce the compound 106. The compound 106 was reacted with lithium bis(trimethylsilyl)amide to form an imine compound and, under a condition of the Lewis acid boron trifluoride-diethyl etherate complex, reacted with the dimsyl anion formed by dimethyl sulfoxide (Me$_2$SO$_2$) and n-butyl lithium (n-BuLi) to furnish the β-amino sulfoxide 107, followed by chiral separation through N-acetyl-L-leucine to obtain the compound 108 having the chiral center, as shown in the following reaction scheme.

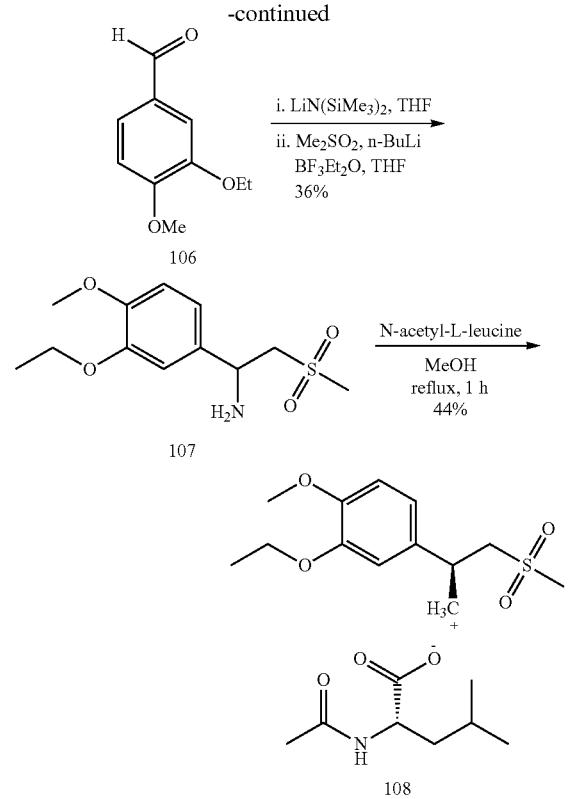

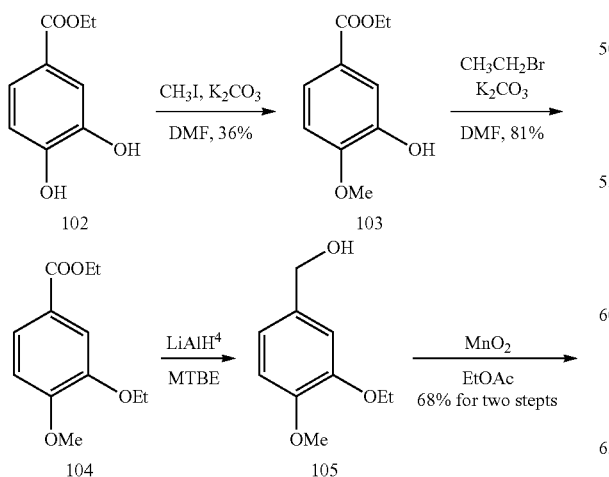

Regarding the other fragment, it is first to reduce the nitro group of the 3-nitrophthalic acid 109 to an amino group through hydrogenation, and then heated in acetic anhydride to reflux so that the phthalic acid is undergone the cyclization reaction and the amino group is acetylated to form the compound 111. At last, the compound 111 and the compound 108 are heated in glacial acetic acid to reflux. The amino group on the compound 108 and the succinic anhydride group are undergone the ring-open reaction and cyclization reaction to furnish the target product Apremilast, as shown in the following reaction scheme.

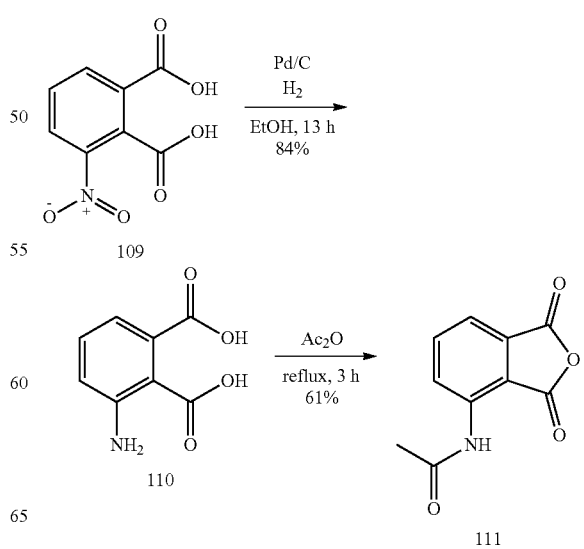

3
-continued

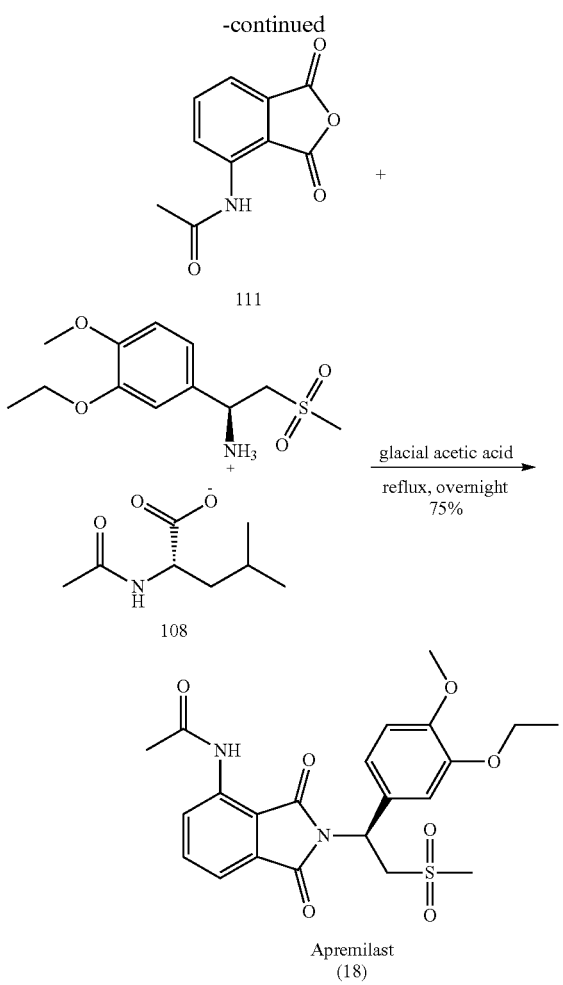

108

Apremilast (18)

However, the protocatechuic acid ethyl ester 102 is not cheap (25 g 75 USD, TCI) and the yield of methylation is only 36%. In addition, due to the feature of chial separation, the yield of this reaction will be lost for half at least, which results in the decrease of the efficiency. N-acetyl-L-leucine is not cheap and needed to be supplied in the amount of equivalent scale. These are quite imperfections of the synthetic steps. Hence, the present invention would like to improve these.

SUMMARY OF THE INVENTION

The primary objective of the present invention is to provide a method for synthesizing the apremilast more efficiently. Addition products are obtained from β-phthalimino vinylsulfones thorough an asymmetric addition reaction, and the obtained addition products are transformed to the drug of apremilast thorough simple reactions.

Hence, the present invention discloses a method for preparation of apremilast, which comprises: a) asymmetric addition reaction: reacting a β-phthalimino vinylsulfone with a nucleophile at a specific temperature in a reaction environment comprising an asymmetric reagent to form a product, and b) acetylation reaction: acetylating said product to obtain the apremilast. Therefore, the present application can obtain the drug of apremilast merely through simple reactions and steps.

In one embodiment, the asymmetric reagent is an asymmetric metal reagent.

4

In one embodiment, the asymmetric metal reagent is formed with a metal reagent and an asymmetric ligand.

In one embodiment, the asymmetric metal reagent is a metal Rh(I)-catalyst.

In one embodiment, the reaction environment comprises a solvent.

In one embodiment, the solvent is an alcoholic solvent.

In one embodiment, the solvent is methanol.

In one embodiment, the reaction environment comprises an additive.

In one embodiment, the additive is a basic reagent.

In one embodiment, the basic reagent is triethylamine.

In one embodiment, the metal reagent and the asymmetric ligand can be in catalytic amounts.

In one embodiment, the catalytic amount of the metal reagent is 5 mol %, and the addition amount of the asymmetric ligand is 6 mol %.

In one embodiment, the specific temperature is from 0 to 150° C.

In one embodiment, the specific temperature is about 60° C.

In one embodiment, the β-phthalimino vinylsulfone is

In one embodiment, the asymmetric ligand is an asymmetric diene.

In one embodiment, the asymmetric diene is wherein Ar is selected from one of the following groups: phenyl ($C_6H_5$), 4-methylphenyl (4-Me-$C_6H_4$), 2-naphthyl, 1-naphthyl, biphenylyl (Ph-$C_6H_4$) tert-butylphenyl (t-Bu-$C_6H_4$), 4-fluorophenyl (4-F—$C_6H_4$), 4-chlorophenyl (4-Cl—$C_6H_4$) and 4-nitrophenyl (4-$NO_2$—$C_6H_4$).

In one embodiment, the Ar of the asymmetric diene is a phenyl group.

In one embodiment, the nucleophile is a boronic acid.

In one embodiment, the boronic acid is

In one embodiment, the equivalent ratio of the β-phthalimino vinylsulfone, the boronic acid and the triethylamine is 1:3:1.

In one embodiment, the asymmetric ligand is

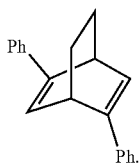

In one embodiment, the equivalent ratio of the β-phthalimino vinylsulfone, the boronic acid and the triethylamine is 1:2:1.

In one embodiment, the product is

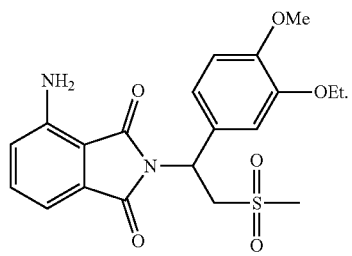 [SMILES: CCOc1cc(C(CS(C)(=O)=O)N2C(=O)c3cccc(N)c3C2=O)ccc1OC]

In one embodiment, the product is S-form.

In one embodiment, the acetylation reaction is to stir a mixture of the product and an acetic anhydride ($Ac_2O$) at 70° C. for three hours.

In summary, the present invention will be described with the following specific embodiments in detail. The following embodiments are used for exemplification without limiting the scope of the present invention. The person ordinarily skilled in the art may easily acknowledge that substantially same results can be obtained from changing or adjusting various non-critical factors.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

Figure 1:
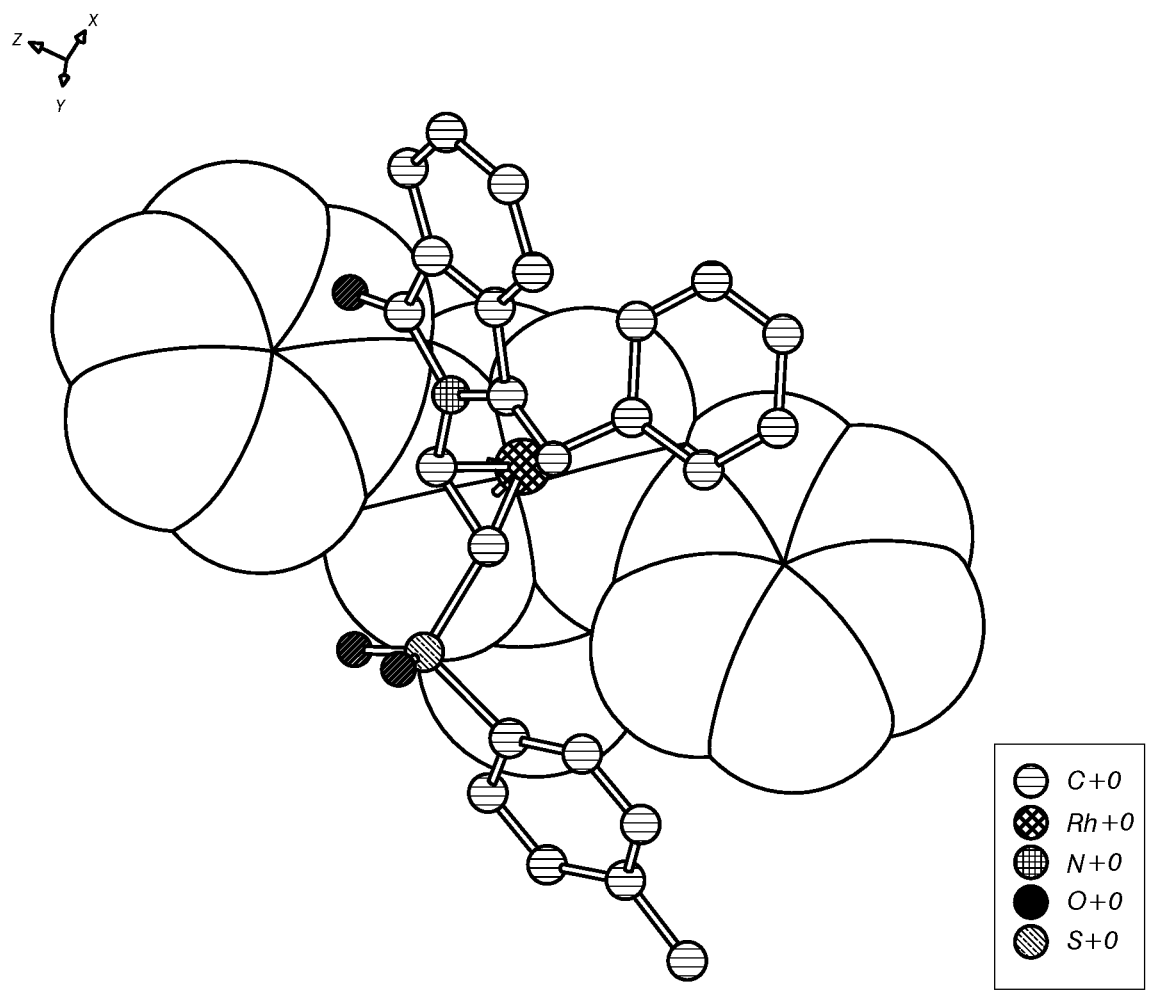
FIG. 1 shows the configuration of the metal Rhodium bonding with the compound 92 of the present invention, ligands and the phenyl groups, which is obtained through calculation and represents the Re face addition at the lowest energy state.

The embodiments of the invention will be apparent from the following detailed description, which proceeds with reference to the accompanying drawings, wherein the same references relate to the same elements.

The present invention provides a method for preparation of the apremilast, which comprises: a) asymmetric addition reaction: reacting a β-phthalimino vinylsulfone with a nucleophile at a specific temperature in a reaction environment comprising an asymmetric reagent to form a product, and b) acetylation reaction: acetylating said product to obtain the apremilast. Therefore, the present invention can synthesize the apremilast more efficiently through a simple reaction.

Furthermore, the asymmetric reagent is an asymmetric metal reagent formed with a metal reagent and an asymmetric ligand, wherein the metal reagent is a Rhodium (which is in +1 oxidation state, Rh(I)) reagent. The present invention will be described as below in detail.

Synthesis of Chiral Diene Ligands:

For the present invention, a natural chiral product, L-bornyl acetate 80, was used as a starting material. Chromium trioxide and acetate were added, followed by reflux for 15 hours at 130° C., and the oxidization product, keto acetate 81, was obtained (yield 35%). The compound 81 was dissolved in ethanol and added with potassium hydroxide to reacting for 11 hours, to obtain the saponification product keto alcohol 82. The keto alcohol 82 was oxidized with pyridinium chlorochromate for 15 hours to obtain diketone 83. The two-step yield was 83%. The compound 83 and the Comins' reagent were dissolved in tetrahydrofuran (THF). Bistriflate 85 was obtained through ditriflate formation by adding KHMDS (potassium bis(trimethylsilyl)amide) in the solution and reacting for two hours at −78° C. (yield 91%). At last, the compound 85 was reacted with aryl boronic acid and palladium(0) catalyst ($Pd(PPh_3)_4$) through Suzuki-Miyaura cross-coupling reaction to obtain nine diene ligands L1 to L9. Ligands L1 to L6 were used to investigate how the steric effects on the ligands influence the stereo-selectivity, and ligands L7 to L9 were used to investigate how the electronic effects of the ligands influence the stereo-selectivity.

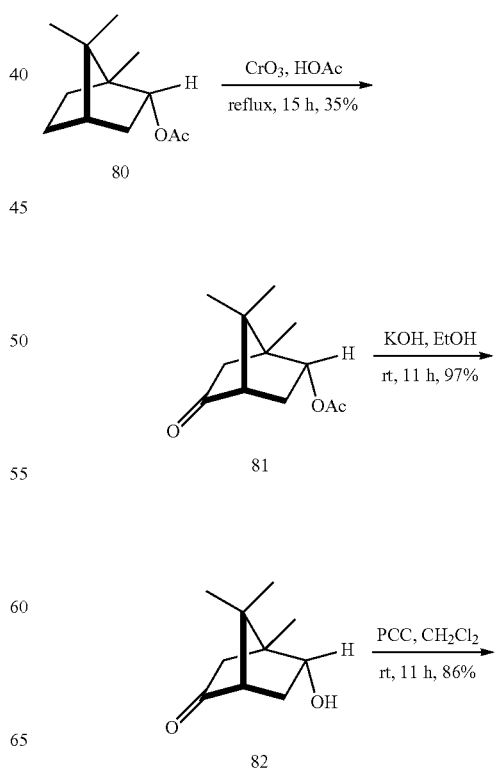

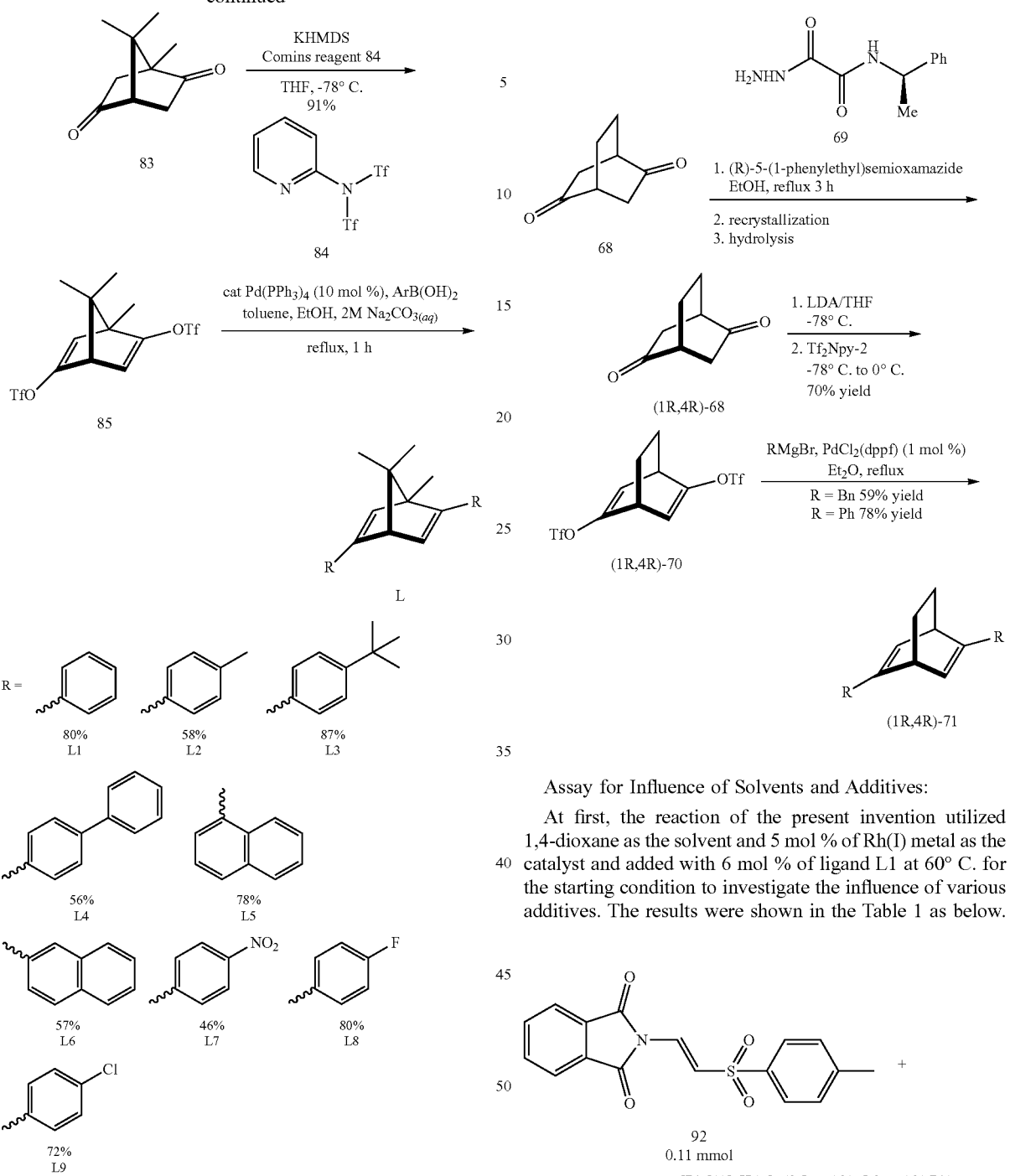

The C₂-symmetric chiral [2.2.2] diene ligand 71 published by Hayashi et. al. in 2004 (Hayashi, T; Tokunaga, N; Otomaru, Y; Ueyama, R; Shintani, R *J. Am. Chem. Soc.* 2004, 126, 13584.) is also used. It was synthesized as below. At first, racemic chiral dione compound 68 was condensed with the compound 69 to form a derivate thereof. The minor diastereomers were separated through recrystallization. The major product was hydrolyzed to obtain the chiral dione compound 68, followed by ditriflate formation and cross-coupling to obtain the chiral diene ligand 71, which is the ligand L10 used in the present invention.

Assay for Influence of Solvents and Additives:

At first, the reaction of the present invention utilized 1,4-dioxane as the solvent and 5 mol % of Rh(I) metal as the catalyst and added with 6 mol % of ligand L1 at 60° C. for the starting condition to investigate the influence of various additives. The results were shown in the Table 1 as below.

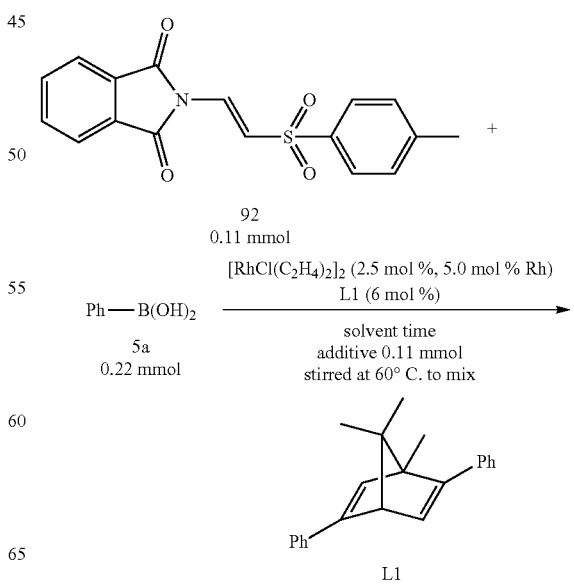

-continued

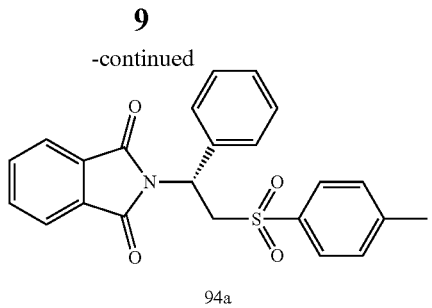

94a

TABLE 1

Influence of solvents and additives

| Entry[a] | Solvent | Additive | Time (h) | Yield (%) | ee (%)[c] |
|---|---|---|---|---|---|
| 1[b] | dioxane | KOH | 6 | 38 | 97 |
| 2 | dioxane | NaOH | 24 | Very messy | N.D.[d] |
| 3 | dioxane | NaHCO$_3$ | 24 | 82 | 99 |
| 4[b] | dioxane | KHF$_2$ | 6 | 51 | 99.6 |
| 5[b] | dioxane | K$_2$CO$_3$ | 6 | 34 | 97 |
| 6 | dioxane | K$_3$PO$_4$ | 10 | 76 | 99 |
| 7[b] | dioxane | NEt$_3$ | 8 | 4 | 98 |
| 8[b] | MeOH | KOH | 18 | 7 | 98 |
| 9 | MeOH | NaHCO$_3$ | 8 | 40 | 97 |
| 10 | MeOH | K$_3$PO$_4$ | 18 | 81 | 97 |
| 11 | MeOH | KHF$_2$ | 8 | 81 | 97 |
| 12 | MeOH | NEt$_3$ | 3 | 96 | 99 |
| 13 | MeOH | DIPA | 6 | 86 | 99 |
| 14 | MeOH | DABCO | 18 | 45 | 98 |
| 15[b] | MeOH | Pyridine | 18 | 38 | 98 |
| 16 | EtOH | NEt$_3$ | 3.5 | 87 | 99 |
| 17[b] | i-PrOH | NEt$_3$ | 24 | 62 | 98 |

In Table 1 as shown above, "[a]" represents the mixture was purified by column chromatography (eluting with 1:3 (v/v) diethyl ether/n-hexane). "[b]" represents NMR yield. "[c]" represents that the values were determined by chiral HPLC analysis. "[d]" represents "not determined."

In Table 1 as shown above, Entries 1 to 7 all demonstrated results with excellent enantiomeric excess (97~99.6% ee). For those additives of inorganic bases, the yields of strong bases (Entries 1 and 2) were not ideal in the cases of potassium hydroxide (KOH) and sodium hydroxide (NaOH), whereas the yields of potassium bifluoride (KHF$_2$) and potassium carbonate (K$_2$CO$_3$) were 51% and 34%, respectively, in which the enantiomeric excess of KHF$_2$ was as high as 99.6%. When sodium bicarbonate (NaHCO$_3$) and potassium phosphate (K$_3$PO$_4$) were used as additives, the yields were good but the reaction times were extended to 24 and 10 hours, respectively (Entries 3 and 6). For those additives of organic bases, it was found that the yield was only 4% when triethylamine (NEt$_3$) was used. The possible cause was lack of proton source. However, it still had an excellent enantiomeric excess. The protic solvent methanol (MeOH) was then used as a solvent to investigate the influence of various additives (Entries 8 to 15). For those additives of inorganic bases, the yield decreased in the case of KOH. The possible cause was that KOH was a strong base and would react with MeOH (Entry 8). However, both yields were good (81%) for potassium phosphate and KHF$_2$ as the additives, and the reaction times were 18 and 8 hours, respectively (Entries 10 and 11). It could be found that the reactivity was worse when the additive had a stronger basicity, in which the obtained yield was best (96%) for the triethylamine whose basicity was weakest, and the enantiomeric excess was as high as 99% ee. Triethylamine was then used as the additive to test the various alcohol solvents (Entries 16 and 17). It was found that the result was best for methanol. It was possible because that methanol was easier to provide a proton. Through the tests for organic bases, organic bases and solvents, triethylamine was determined as the optimal base as the additive and methanol was determined as the optimal solvent.

Assay of Ligand Effects (I):

For Entry 1 in the Table 2 as below, the yield (96%) and the enantiomeric excess (99% ee) were both very good in the case of the phenyl-substituted [2.2.1] ligand L1. The ligands substituted with other aryl groups were then used, such as Entries 2 to 6. The results demonstrated that the obtained yields were lower with the increasing of the size of the aryl groups, whereas the yields were 58% to 92% in the cases of ligands L7, L8 and L9. Accordingly, the yields decreased when the electron-withdrawing effects of the substituents on the phenyl ring increased. According to Table 2, the experimental results demonstrates that the used ligands exhibited excellent stereo-selectivities with 97-99% ee.

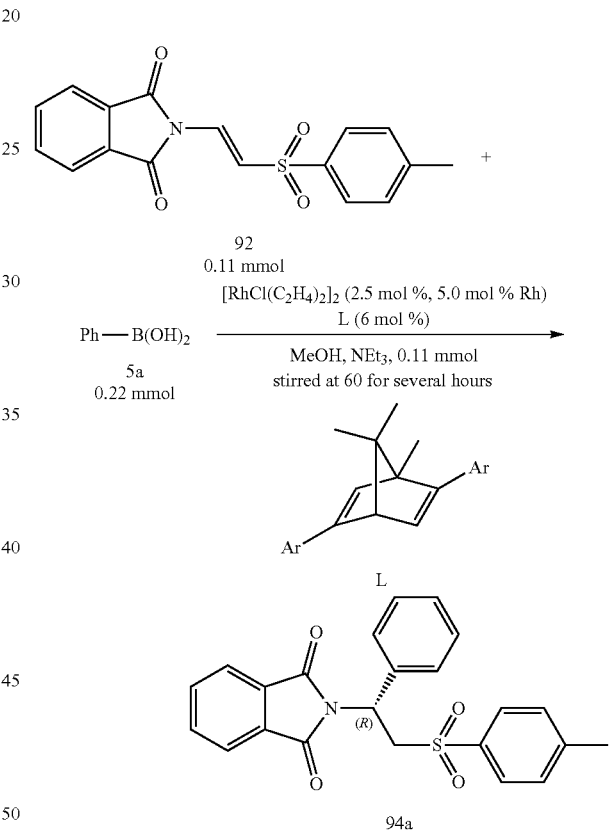

TABLE 2 ligand effects (I)

| Entry[a] | Ar | Time (h) | Yield (%)[b] | ee (%)[c] |
|---|---|---|---|---|
| 1 | C$_6$H$_5$ (L1) | 3 | 96 | 99 |
| 2 | 4-Me—C$_6$H$_4$ (L2) | 3 | 90 | 97 |
| 3 | 2-Na (L6) | 5 | 81 | 99 |
| 4 | 1-Na (L5) | 4.5 | 43 | 97 |
| 5 | Ph—C$_6$H$_4$ (L4) | 4.5 | 83 | 98 |
| 6 | t-Bu—C$_6$H$_4$ (L3) | 4.5 | 89 | 98 |
| 7 | 4-F—C$_6$H$_4$ (L8) | 4.5 | 83 | 98 |
| 8 | 4-Cl—C$_6$H$_4$ (L9) | 3 | 92 | 97 |
| 9 | 4-NO$_2$—C$_6$H$_4$ (L7) | 5 | 58 | 99 |

In Table 2 as shown above, "*a*" represents the mixture was purified by column chromatography (eluting with 1:3 (v/v) diethyl ether/n-hexane). "*b*" represents NMR yield. "*c*" represents that the values were determined by chiral HPLC analysis.

Assay of Ligand Effects (II):

It was found that, in the study shown as Table 3, the chiral center of the obtained product when the chiral bicyclo[2.2.2] diene ligand L10 was used had an opposite configuration with respect to that of the obtained product when the chiral bicyclo[2.2.1] diene ligand L1 was used, whereas both had well yields and enantiomeric excess. However, the expected products could not be produced when the chiral bicyclo [3.3.0] diene ligand L11 and a phosphorus-contained (S)-BINAP ligand L12 were used.

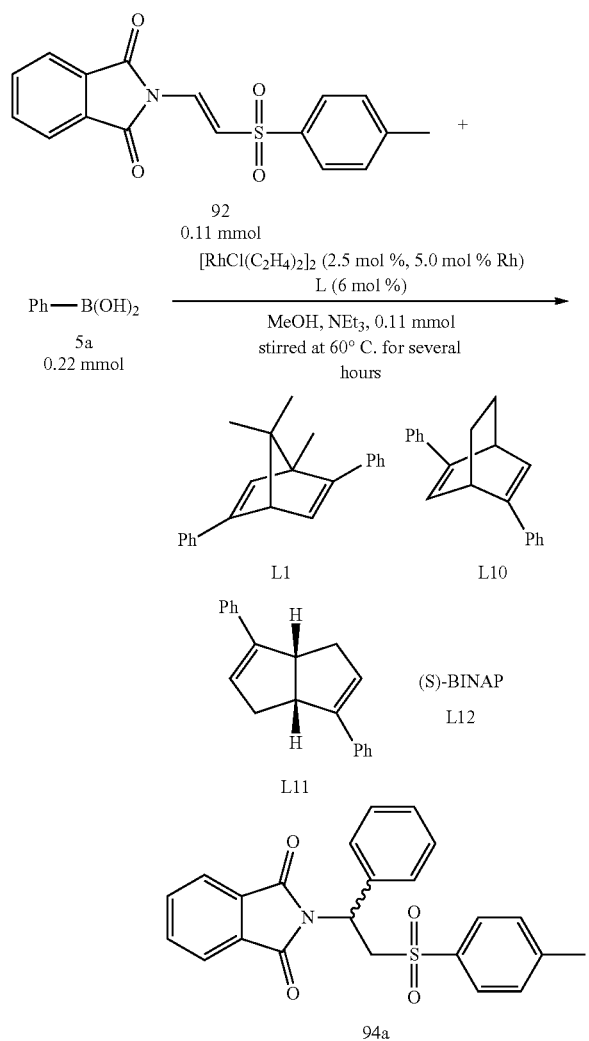

TABLE 3

Analysis of influence of ligands (II)

| Entry[a] | Ligand | Time (h) | Yield (%)[b] | ee (%)[c] |
|---|---|---|---|---|
| 1 | L1 | 2 | 99 | 99 |
| 2 | L10 | 3 | −91 | −98 |
| 3 | L11 | 24 | N.R.[d] | N.D.[e] |
| 4 | L12 | 30 | N.R.[d] | N.D.[e] |

In Table 3 as shown above, "*a*" represents the mixture was purified by column chromatography (eluting with 1:3 (v/v) diethyl ether/n-hexane). "*b*" represents NMR yield. "*c*" represents that the values were determined by chiral HPLC analysis. "*d*" represents "no reaction." "*e*" represents "not determined."

Assay of Temperature Effects:

From Table 4 below, it was found that when the reaction temperature was higher than 60° C., the yields decreased with the increase of temperature (Entries 3 and 4). The primary reason was because that the protondeboronation of a boronic acid was faster at a higher temperature, which resulted in an insufficient amount of boronic acid for completion of the reaction. If the temperature decreased to 30° C., the reaction time increased greatly, which needed 24 hours to complete the experiment (Entry 1). Through the tests of temperature effects, it was determined that 60° C. was optimal for reaction.

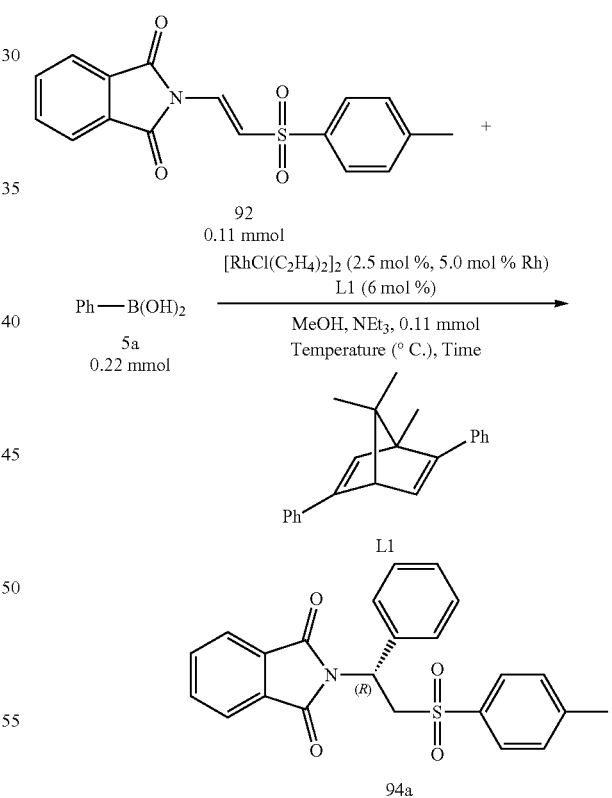

TABLE 4

Temperature effects

| Entry[a] | Temperature (° C.) | Time (h) | Yield (%)[b] | ee (%)[c] |
|---|---|---|---|---|
| 1 | 30 | 24 | 85 | 99 |
| 2 | 60 | 2 | 99 | 99 |

TABLE 4-continued

Temperature effects

| Entry[a] | Temperature (° C.) | Time (h) | Yield (%)[b] | ee (%)[c] |
|---|---|---|---|---|
| 3 | 80 | 1 | 92 | 99 |
| 4 | 100 | 0.5 | 81 | 98 |

In Table 4 as shown above, "[a]" represents the mixture was purified by column chromatography (eluting with 1:3 (v/v) diethyl ether/n-hexane). "[b]" represents isolated yield. "[c]" represents that the values were determined by chiral HPLC analysis.

Assay for Influence of Amounts of the Catalysts:

At last, the catalytic amounts of metal Rhodium were adjusted to test the influence to the present invention caused by various catalytic amounts of metal Rhodium on time, yield and enantiomeric excess. The Table 5 shown as below demonstrated that when the catalytic amounts decreased, the enantiomeric excess slightly decreased whereas the yields significantly decreased and the reaction times increased greatly. Hence, the catalytic amount of Rhodium catalyst was determined as 5 mol % at last.

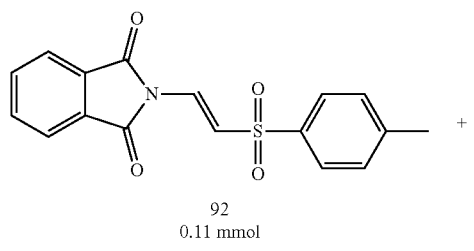

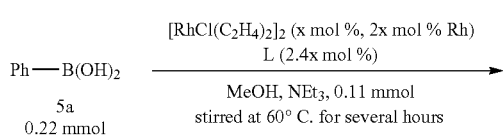

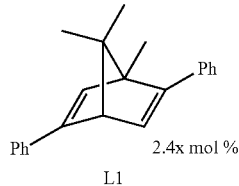

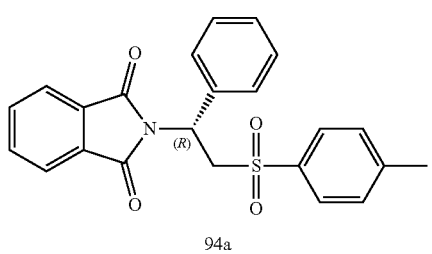

TABLE 5

Influence of catalytic amounts

| Entry[a] | Rh (mol %) | Time (h) | Yield (%)[b] | ee (%)[c] |
|---|---|---|---|---|
| 1 | 5 | 2 | 99 | 99 |
| 2 | 3 | 7 | 89 | 98 |
| 3 | 1 | 24 | 50 | 96 |

In Table 5 as shown above, "[a]" represents the mixture was purified by column chromatography (eluting with 1:3 (v/v) diethyl ether/n-hexane). "[b]" represents isolated yield. "[c]" represents that the values were determined by chiral HPLC analysis.

From the above-mentioned assays, the embodiment with optimized conditions is as follow. β-phthalimino vinylsulfones are reacted through the asymmetric reaction with 5 mol % of the metal Rhodium reagent, 6 mol % of ligand L1 in the solvent of methanol with triethylamine as an additive, boronic acids as nucleophiles, and at 60° C. The reaction scheme is:

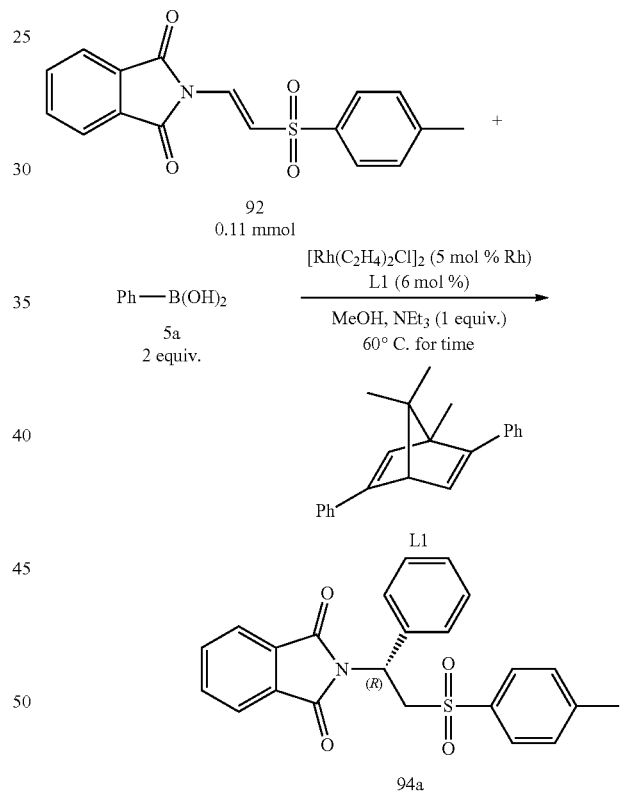

A series of asymmetric addition reactions with boronic acids in optimized conditions (I):

β-phthalimino vinylsulfones were reacted with various aromatic boronic acids through the asymmetric addition reactions in the optimized conditions to investigate the yields and enantiomeric excess. The results shown in Table 6 as below demonstrated that the enantiomeric excess was excellent for all cases (94% to 99%). The yield of aryl boronic acids having electron acceptors was similar with that of the aryl boronic substituted with alkyl groups (Entries 2 to 10), and the yield of the aryl boronic acid having a substituent on 2-position decreased because of steric hindrance (Entries 2 and 9). The enantioselectivity was 99% ee for each case. The aryl boronic acids with substituents on 3- or 4-positions did not show much difference. However, when chlorine is substituted on 3-position, the yield decreased to 62% (Entry 12), which could be attributed to chlorine was a large substituent and thus had a greater steric hindrance. It was noteworthy that the results were still acceptable for those aryl boronic acids substituted with aromatic groups (Entries 8 to 10), even those aromatic groups having a large steric hindrance. It was speculated that the aromatic fragments having more π-electrons were easier to transfer from the aryl boronic acids to the metal Rhodium to form a Rhodium-aryl complex [Rh—Ar]. The obtained yields were well for those aryl boronic acid with electron acceptors (Entries 11 and 13), but the reaction times were slightly extended. However, then the electron-withdrawing effects were strong (Entries 14 and 16), the yields decreased significantly. The primary reason for the significant decrease of yields was that the activity of the boronic acids toward the addition reaction decreased, which resulted in more protodeboronation.

Because the steric center of the addition product using the [2.2.2] diene ligand L10 had an opposite configuration with respect to that using the ligand L1, the Apremilast could be synthesized accordingly. Therefore, Table 6 also demonstrated the result of the test using ligand L10 to study its effect on boronic acids in addition reactions. It was found that the enantiomeric excess was excellent for all cases, and the yields were similar with ligand L1. It was noteworthy that the addition reaction was faster for [2.2.2] diene ligand L10, and the several cases of those boronic acids with larger steric hindrance had increased yields (Entries 2, 9 and 14).

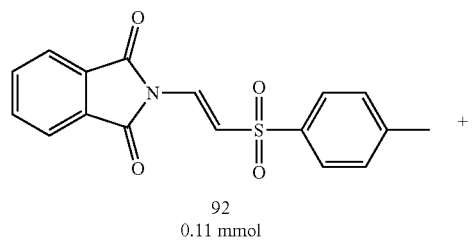

92
0.11 mmol

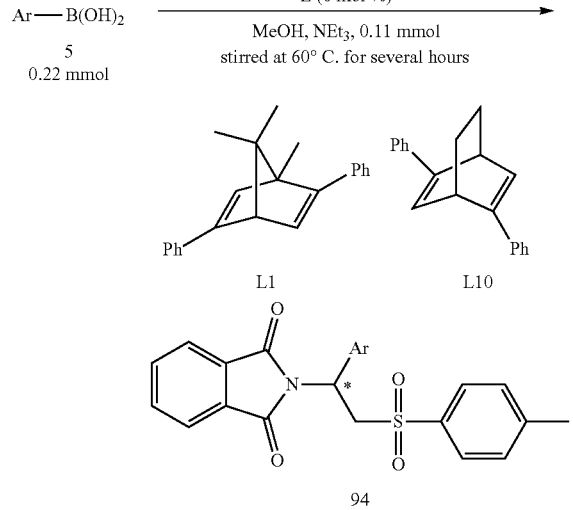

94

TABLE 6

A series of asymmetric addition reaction with boronic acids in optimized conditions (I)

| | | L1 | | | L10 | | |
|---|---|---|---|---|---|---|---|
| Entry[a] | Ar | Time (h) | Yield (%)[b] | ee (%)[c] | Time (h) | Yield (%)[b] | ee (%)[c] |
| 1 | C$_6$H$_5$ (5a) | 2 | 99 (94a) | 99 | 3 | 91 (94a) | −96 |
| 2 | 2-OMe—C$_6$H$_4$ (5b) | 6 | 38 (94b) | 99 | 3 | 51 (94b) | −98 |
| 3 | 3-OMe—C$_6$H$_4$ (5c) | 3.5 | 85 (94c) | 96 | 2 | 82 (94c) | −97 |
| 4 | 4-OMe—C$_6$H$_4$ (5d) | 5.5 | 87 (94d) | 97 | 4 | 80 (94d) | −96 |
| 5 | 3-Me—C$_6$H$_4$ (5e) | 5 | 88 (94e) | 98 | 3 | 83 (94e) | −97 |
| 6 | 4-Me—C$_6$H$_4$ (5f) | 5 | 87 (94f) | 95 | 4 | 63 (94f) | −97 |
| 7 | 4-t-Bu—C$_6$H$_4$ (5g) | 5 | 81 (94g) | 94 | 3 | 76 (94g) | −95 |
| 8 | biph (5h) | 3.7 | 95 (94h) | 98 | 3 | 91 (94h) | −96 |
| 9 | 1-Np (5i) | 5 | 70 (94i) | 99 | 2 | 84 (94i) | −98 |
| 10 | 2-Np (5j) | 3.7 | 90 (94j) | 95 | 3 | 81 (94j) | −96 |
| 11 | 4-F—C$_6$H$_4$ (5k) | 6 | 85 (94k) | 98 | 2 | 88 (94k) | −97 |
| 12 | 3-Cl—C$_6$H$_4$ (5l) | 8 | 62 (94l) | 97 | 3 | 54 (94l) | −98 |
| 13 | 4-Cl—C$_6$H$_4$ (5m) | 8 | 80 (94m) | 97 | 2 | 96 (94m) | −98 |
| 14 | 3-CF$_3$—C$_6$H$_4$ (5n) | 48 | 37 (94n) | 97 | 3 | 67 (94n) | −98 |
| 15 | 4-CF$_3$—C$_6$H$_4$ (5o) | 30 | 84 (94o) | 98 | 2 | 84 (94o) | −98 |
| 16 | 4-CN—C$_6$H$_4$ (5p) | 48 | 24 (94p) | 99 | 48 | 19 (94p) | −95 |

In Table 6 as shown above, "[a]" represents the mixture was purified by column chromatography (eluting with 1:3 (v/v) diethyl ether/n-hexane). "[b]" represents isolated yield. "[a]" represents that the values were determined by chiral HPLC analysis.

Asymmetric Addition Reaction with Starting Compounds in Cis Form

In the Table 7 as shown below, the starting compound 95 in (Z)-form was used. It was hoped that the chiral center of the product can be controlled by changing the configuration of the starting material, and that Apremilast could be synthesized without using ligand L10. However, the product obtained at 60° C. was still in R-form. This was because when the (Z)-form starting compound 95 was heated, its structure would be first converted to (E)-form, which is more thermodynamically stable, and then continue to undergo the asymmetric addition reaction. When the reaction temperature was 30° C., the starting compound would not be converted, but the steric hindrance of (Z)-form was too large so that no product was produced.

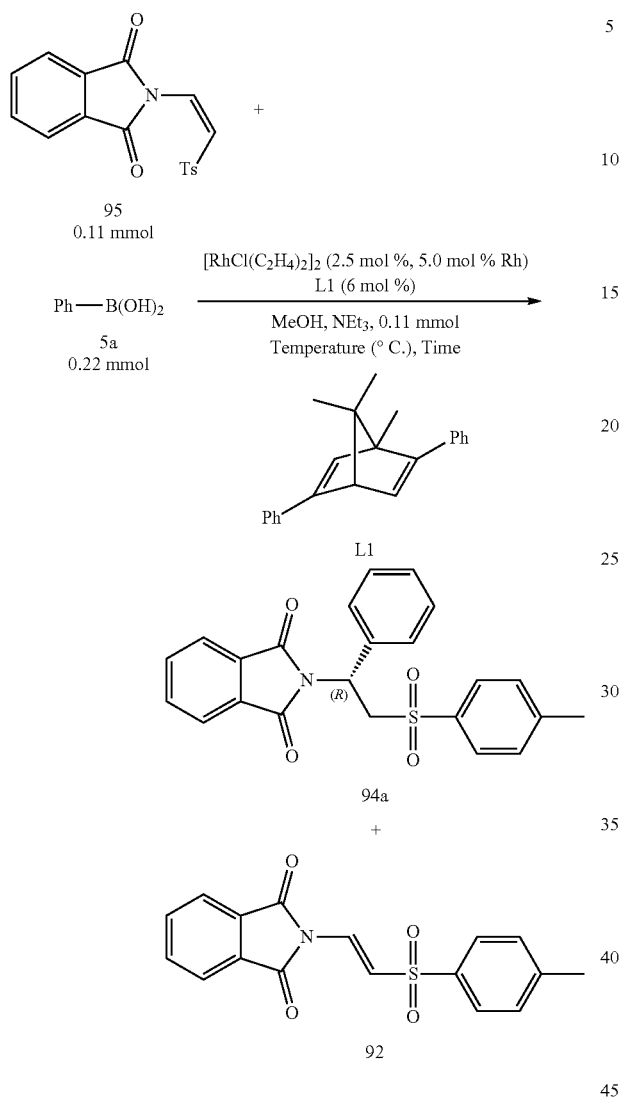

A series of asymmetric addition reactions with boronic acids in optimized conditions (II):

The starting compound 96 which was a β-phthalimino vinylsulfone bearing a long carbon chain functional group was then used to react with various aryl boronic acids (Table 8). In the result, the yields obviously decreased. From FIG. 1, it could be acknowledged that the sulfonyl group was away from the metal Rhodium during the addition reaction. Therefore, its steric hindrance would not interfere this reaction. The decrease of the yields may be attributed to the reduction of the electron-withdrawing effect of the sulfonyl group due to the long carbon chain, which in turn resulted in the decrease of the reactivity of the compound 96. The enantiomeric excesses remained at very high levels (95%-97%).

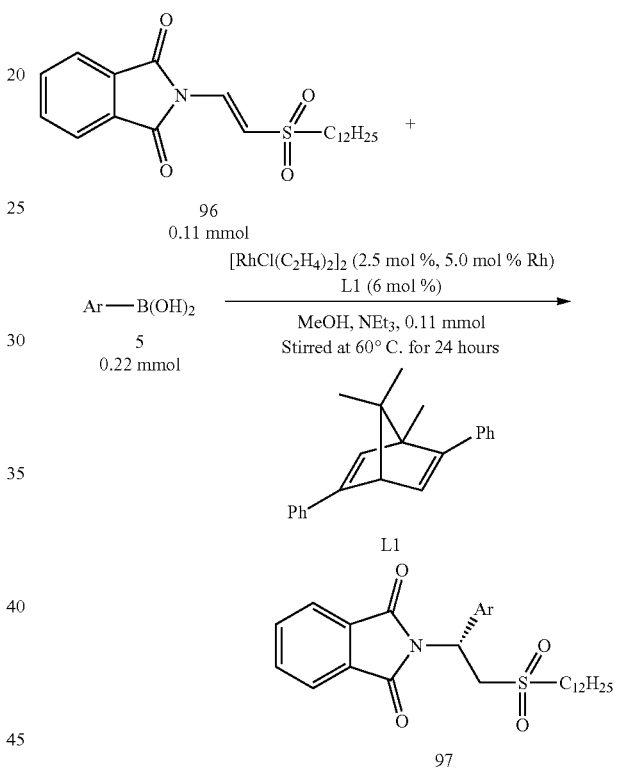

TABLE 7 asymmetric addition reaction with starting compound in (Z)-form

| Entry[a] | Temperature (° C.) | Time (h) | Yield (%)[b] | ee (%)[c] |
|---|---|---|---|---|
| 1 | 60 | 3 | 80 (94a) | 94 |
| 2 | 30 | 24 | 0 (trans form S.M.) | NA[d] |

In Table 7 as shown above, "[a]" represents the mixture was purified by column chromatography (eluting with 1:3 (v/v) diethyl ether/n-hexane). "[b]" represents isolated yield. "[c]" represents that the values were determined by chiral HPLC analysis. "[d]" represents "not analyzed."

Figure 2:
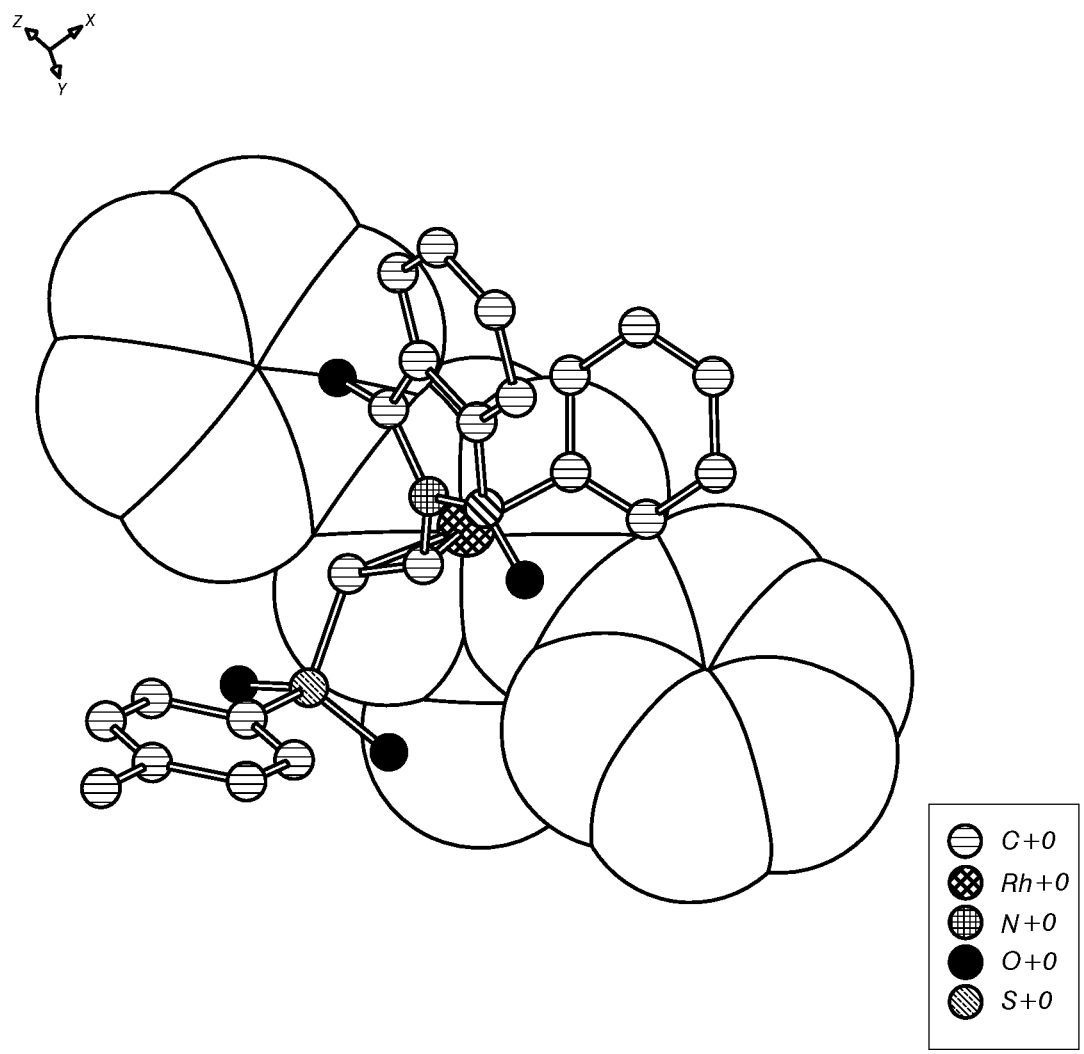
FIG. 2 shows the configuration of the metal Rhodium bonding with the compound 92 of the present invention, ligands and the phenyl groups, which is obtained through calculation and represents the Si face addition at the lowest energy state.

The configurations of metal Rhodium bonding with the compound 92, the ligand and the phenyl group as shown in FIGS. 1 and 2 are obtained through calculations, which represent Re face addition and Si face addition, respectively, at the lowest energy state. From FIG. 1, it could be observed that the sulfonyl group was away from the metal Rhodium, and the phthalimino group was near the metal Rhodium.

TABLE 8

A series of asymmetric addition reactions with boronic acids in optimized conditions (II)

| Entry[a] | Ar | Time (h) | Yield (%)[b] | ee (%)[c] |
|---|---|---|---|---|
| 1 | C$_6$H$_5$ (5a) | 24 | 77 (97a) | 96 |
| 2 | 4-t-Bu—C$_6$H$_4$ (5g) | 24 | 47 (97g) | 95 |
| 3 | 4-F—C$_6$H$_4$ (5k) | 24 | 57 97k) | 97 |

In Table 8 as shown above, "[a]" represents the mixture was purified by column chromatography (eluting with 1:3 (v/v) diethyl ether/n-hexane). "[b]" represents isolated yield. "[c]" represents that the values were determined by chiral HPLC analysis. "[d]" represents "not analyzed."

A Series of Asymmetric Addition Reactions with Boronic Acids in Optimized Conditions (III):

In the Table 9 as shown below, the starting compound 98 which was a β-phthalimino vinylsulfone bearing succinimide was used to react with various aryl boronic acids. The yields for all decreased to 40%-50%. This was because, under conditions of this experiment, methanol would react with the amide group in the succinimide through the ring-open reaction. Similarly, the obtained enantiomeric excesses were very good (93%-96%) in this experiment.

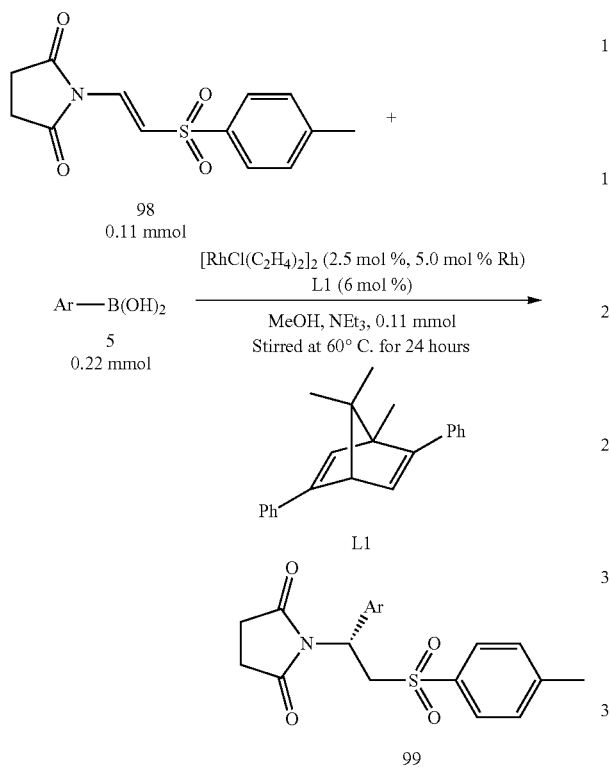

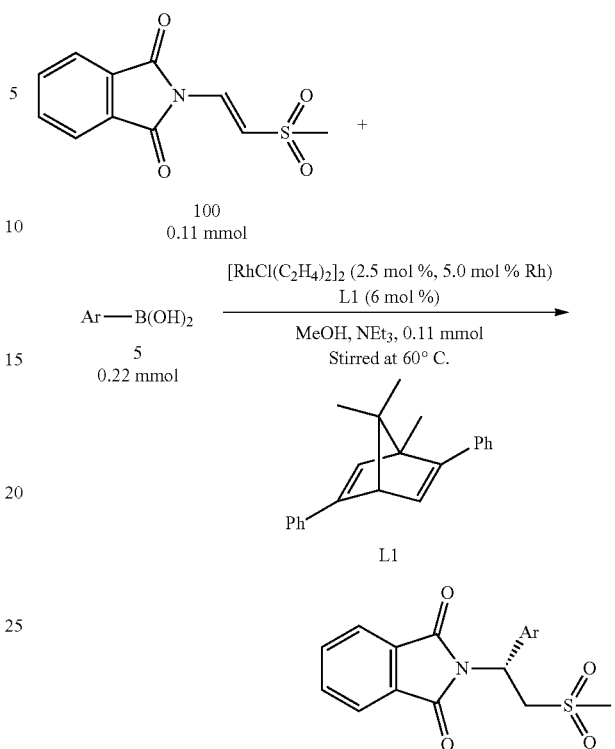

TABLE 9

A series of asymmetric addition reactions with boronic acids in optimized conditions (III)

| Entry[a] | Aryl | Time (h) | Yield (%)[b] | ee (%)[c] |
|---|---|---|---|---|
| 1 | C$_6$H$_5$ (5a) | 4 | 48 (99a) | 96 |
| 2 | 4-OMe—C$_6$H$_4$ (5d) | 4 | 43 (99d) | 93 |
| 3 | 4-t-Bu—C$_6$H$_4$ (5g) | 4 | 42 (99g) | 96 |
| 4 | 4-F—C$_6$H$_4$ (5k) | 4 | 47 (99k) | 96 |

In Table 9 as shown above, "[a]" represents the mixture was purified by column chromatography (eluting with 1:3 (v/v) diethyl ether/n-hexane). "[b]" represents isolated yield. "[c]" represents that the values were determined by chiral HPLC analysis.

A Series of Asymmetric Addition Reactions with Boronic Acids in Optimized Conditions (IV):

At last, the compound 100 which was a β-phthalimino vinylsulfone bearing a mesyl group was used as the starting material to react with various boronic acid reagents through the addition reaction. The enantiomeric excesses were 96%-98%. The yields of Entries 2 and 3 were 55% and 72%, respectively. The reason for the unsatisfactory yields was similar with Table 8. The electron-withdrawing effect of the mesyl group is weaker than the tosyl group, resulting in the inferior reactivity of the compound 100.

TABLE 10

A series of asymmetric addition reactions with boronic acids in optimized conditions (IV)

| Entries[a] | Aryl | Time (h) | Yield (%)[b] | ee (%)[c] |
|---|---|---|---|---|
| 1 | C$_6$H$_5$ (5a) | 1.5 | 94 (101a) | 98 |
| 2 | 4-OMe—C$_6$H$_4$ (5d) | 2 | 55 (101d) | 96 |
| 3 | 4-t-Bu—C$_6$H$_4$ (5g) | 2 | 72 (101g) | 97 |

In Table 10 as shown above, "[a]" represents the mixture was purified by column chromatography (eluting with 1:3 (v/v) diethyl ether/n-hexane). "[b]" represents isolated yield. "[c]" represents that the values were determined by chiral HPLC analysis.

Application of Synthesis

The first part of the application of synthesis was to synthesize the nucleophilic boronic acids, as shown in the reaction scheme below:

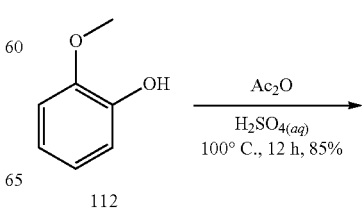

-continued

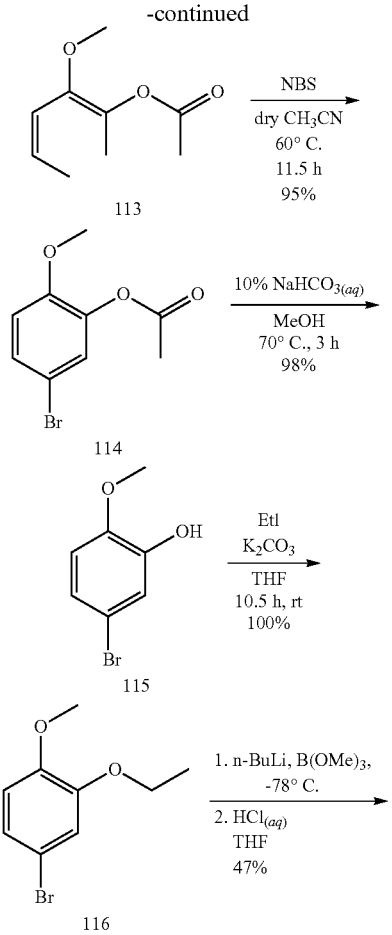

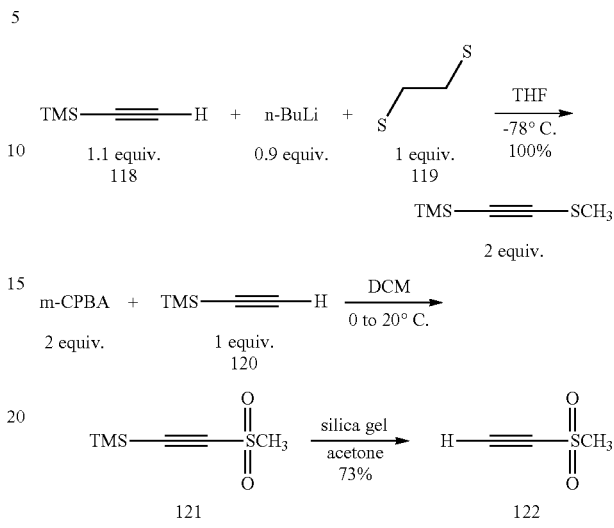

121. The protecting trimethylsilyl group was removed from the compound 121 through the acid property of silica gel to produce the compound 122.

The third part was to synthesize the starting compound β-phthalimino vinylsulfone, as shown in the following reaction scheme. The catalyst Pd/C was used to reduce the nitro compound 92 to the amine compound 89 through hydrogenation. After successfully producing the compound 89, the compound 89 was reacted with the compound 90 through addition reaction, under the condition of 4-Dimethylaminopyridine (DMAP) as a base and at 50° C. After three days, the thermodynamically stable trans compound was obtained as the single product 88. At last, the product 88 was acetylated to form the β-phthalimino vinylsulfone 87.

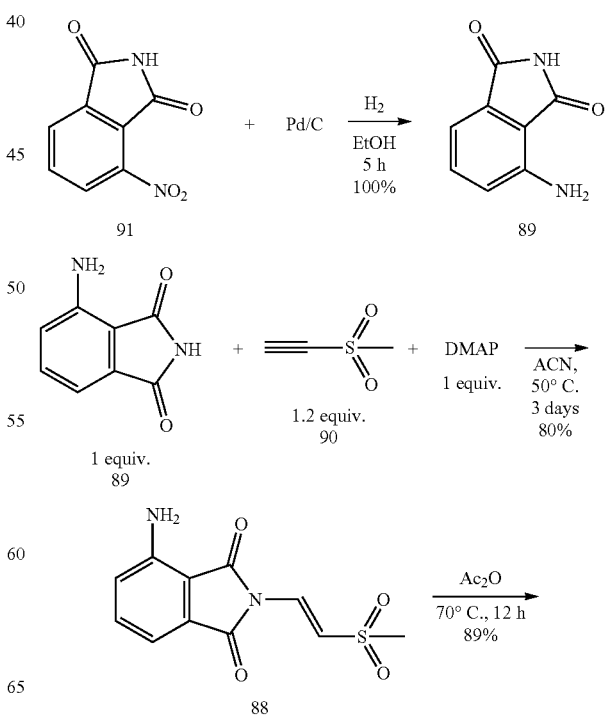

The hydroxyl group of the 2-methoxyphenol was first acetylated to lower the ability of electrophilic aromatic substitution on 4-position, avoiding the formation of by-products. N-bromosuccinimide (NBS) was then used to selectively conjugate the bromine atom on the 3-position through bromination, followed by hydrolysis of the acetyl group under a basic condition and reacting with diiodoethane to furnish the ethoxy compound 116. The compound 116 was reacted with n-butyl lithium (n-BuLi) and trimethyl borate to form a boronic ester. At last, the target product of boronic acid 117 was obtained through hydrolysis with hydrogen chloride.

The second part was to synthesize the sulfonyl alkyne molecular fragment, as shown in the reaction scheme below. The n-BuLi and trimethylsilylacetylene were used for deprotonation and then reacted with dimethyl sulfide through substitution reaction to furnish the compound 120, followed by treating with meta-chloroperoxybenzoic acid (m-CPBA) to oxidize the sulfide compound to furnish the compound -continued

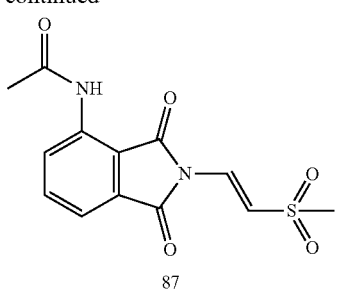

87

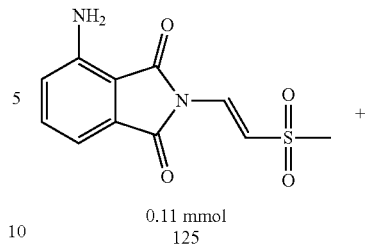

0.11 mmol
125

After obtaining the β-phthalimino vinylsulfone 87 and the boronic acid 117, the last step was to synthesize the racemic apremilast with the optimized conditions. However, this time the experiment results showed that no expected product 18 was formed at all, but the by-product 123 of twice addition was formed instead. In addition, the amount of the by-product 123 increased with the addition amount of the boronic acid, as shown in the Table 11 below. It was speculated that the primary reason for the formation of the by-product was not the boronic acid but the nitrogen-containing substitute on the β-phthalimino vinylsulfone 87.

TABLE 11

Influence of temperature, solvent, and additive effect to the metal Rhodium on racemic addition reaction

| Entry | Temperature (° C.) | 117 (equiv.) | Time (h) | Solvent | Additive | Yield of 18 (%) | Yield of 123 (%) |
|---|---|---|---|---|---|---|---|
| 1 | 60 | 2 + 2 | 2 + 1 | MeOH | NEt₃ | 0 | 91 |
| 2 | 60 | 2 | 2 | MeOH | NEt₃ | 7 | 81 |
| 3 | 23 | 1 | 2 | MeOH | NEt₃ | 0 | 14 |
| 4 | 0 | 1 | 24 | MeOH | NEt₃ | 10 | 7 |
| 5 | 23 | 1 | 24 | MeOH | KHF₂ | 0 | 4 |
| 6 | 23 | 1 | 20 | Dioxane | K₃PO₄ | 0 | 5 |

In the Table 11 as shown above, generally the β-phthalimino vinylsulfone 87 (0.11 mmol), boronic acid 117 (0.23 mmol), [Rh(C$_2$H$_4$)$_2$Cl]$_2$ (2.5 mol %), and NEt$_3$ (0.11 mmol) in MeOH (2 mL) were stirred for several hours at 60° C. The solution was removed under vacuum. The residue was purified by column chromatography (Hexanes/Acetone=5/1) to furnish the target product.

The β-phthalimino vinylsulfone 125 without substitution on the nitrogen was used as the starting compound for asymmetric addition reaction, as shown in the reaction scheme below. This time the experiment results showed that the isolated yield was 41%. The boronic acid was supplied twice in this experiment. It was found that the amount of product was obviously increased after the first supplement of 1 equivalent amount of boronic acid, and not by-product was formed at all. However, when two equivalent amount of boronic acid was one-time supplied for a second time, the by-product was formed in a large amount. In other words, the equivalent amount of single supplement of boronic acid should be controlled carefully.

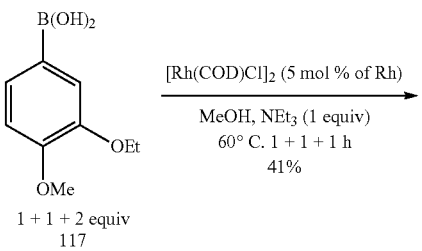

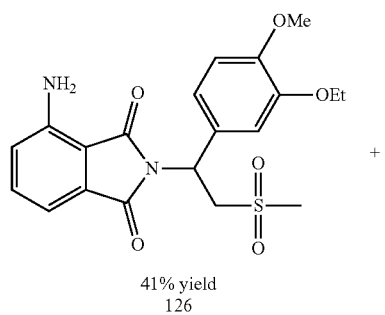

41% yield
126

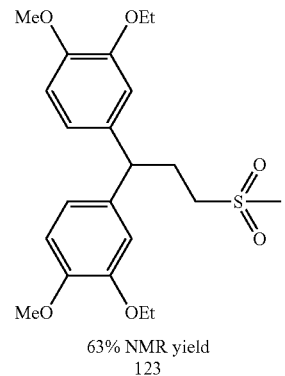

63% NMR yield
123

The Table 12 as below demonstrated that the boronic acid should be supplied twice for the asymmetric addition reaction using the ligand L1, the β-phthalimino vinylsulfone 125 and the boronic acid 127, and the yield was as high as 95%. Instead, when using the ligand L10, the boronic acid only had to be supplied for single time but the yield was 83%. Although the reaction efficiency was increased, but 24% by-product was produced. Because the apremilast was a S-form compound and for large-scale production, 10 g of the ligand L10 was reacted with 1 g of the β-phthalimino vinylsulfone 125 through asymmetric addition reaction in Entry 3. The result was as good as Entry 2.

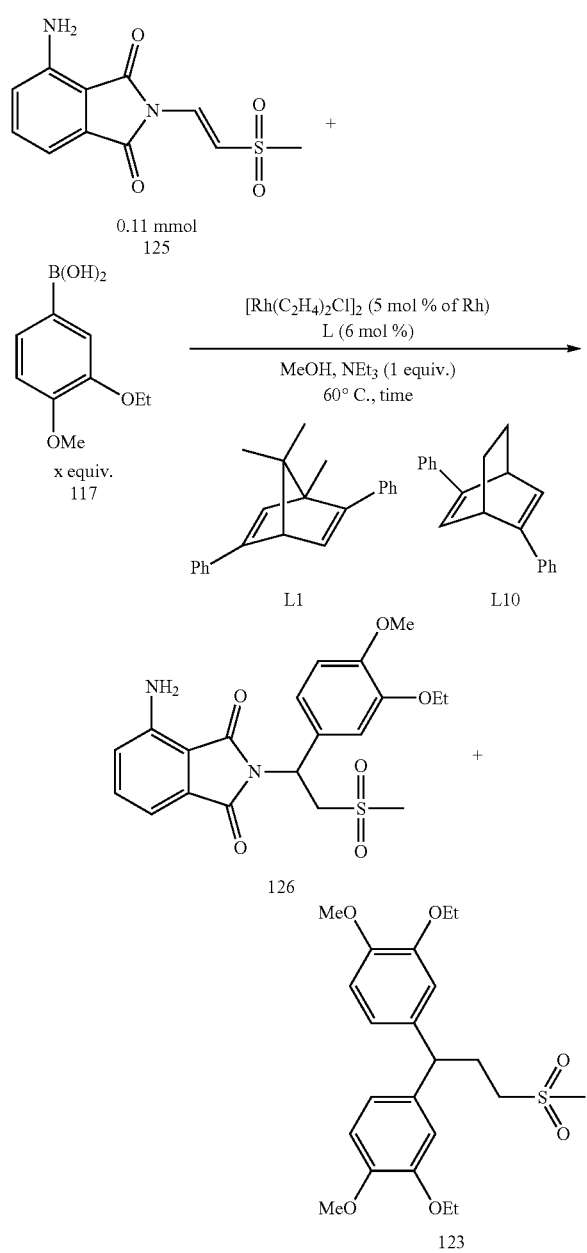

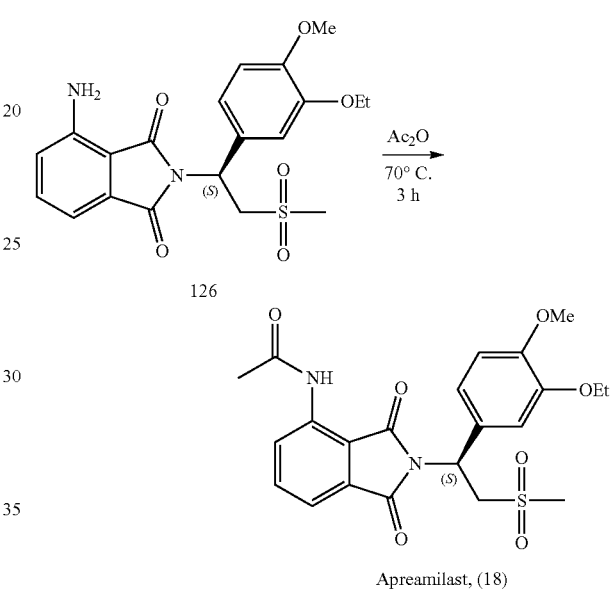

Apreamilast, (18)

tography (eluting with 100:2 (v/v) DCM/MeOH). "$^c$" represents the reaction conditions wherein the β-phthalimino vinylsulfone 125 (3.8 mmol), boronic acid 117 (7.5 mmol), [Rh(C$_2$H$_4$)$_2$Cl]$_2$ (2.5 mol %, 5.0 mol % of Rh), ligand L10 (6 mol %) and NEt$_3$ (3.8 mmol) in MeOH were stirred for several hours at 60° C.

At last, the S-form addition product 126 was acetylated to successfully furnish the Apremilast 18, with yield of 97% and enantiomeric excess of 98%. Entry 3 demonstrated a result which amplify the amount of the starting compound to 3.1 mmol, with yield of 94% and enantiomeric excess of 97%. A good result was also obtained by acetylating the R-form Apremilast precursor (Entry 1 in Table 13), with yield of 98% and enantiomeric excess of 96%.

TABLE 13

Acetylation reaction

| Entry$^a$ | Chiral center | Yield (%)$^b$ | ee (%)$^c$ |
| --- | --- | --- | --- |
| 1 | R form | 98 | 96 (R) |
| 2 | S form | 97 | 98 (S) |
| 3$^d$ | S form | 94 | 97 (S) |

In Table 13 as shown above, "$^a$" represents the conditions wherein the Apremilast precursor 126 was stirred in acetic anhydride for three hours at 70° C. "$^b$" represents that the mixture was purified by column chromatography (eluting with 1:1 (v/v) EA/n-hexane). "$^c$" represents that the values were determined by chiral HPLC analysis. "$^d$" represents the amount of the Apremilast precursor 126 was 3.1 mmol.

In summary, the present invention discloses a method for preparation of Apremilast. β-phthalimino vinylsulfones are reacted with aryl boronic acids with the Rh catalyst through asymmetric aryl addition reaction, and the chiral center is controlled by the selection of the ligand. The obtained addition product can furnish the drug Apremilast through simple reaction. It is a more efficient method for synthesizing Apremilast.

Although the invention has been described with reference to specific embodiments, this description is not meant to be construed in a limiting sense. Various modifications of the

TABLE 12

Asymmetric addition reaction of β-phthalimino vinylsulfone 125

| Entry | Ligand | 117 (equiv.) | Time (h) | Yield of 126 (%)$^b$ | Yield of 123 (%)$^b$ | Chiral center |
| --- | --- | --- | --- | --- | --- | --- |
| 1$^a$ | L1 | 1 + 1 + 1 | 1 + 1 + 1 | 95 | 0 | R form |
| 2$^a$ | L10 | 1 + 1 | 1 + 1 | 83 | 24 | S form |
| 3$^c$ | L10 | 1 + 1 | 1 + 1 | 85 | 26 | S form |

In Table 12 as shown above, "$^a$" represents the conditions wherein the β-phthalimino vinylsulfone 125 (0.11 mmol), boronic acid 117 (0.22 mmol), [Rh(C$_2$H$_4$)$_2$Cl]$_2$ (2.5 mol %, 5.0 mol % of Rh), ligand (6 mol %) and NEt$_3$ (0.11 mmol) in MeOH were stirred for several hours at 60° C. "$^b$" represents that the mixture was purified by column chroma-

What is claimed is:

1. A method for preparation of Apremilast, comprising:
   a) asymmetric addition reaction: reacting a β-phthalimino vinylsulfone with a nucleophile at a specific temperature in a reaction environment comprising an asymmetric reagent to form a product, wherein the nucleophile has a para-methoxy/meta-ethoxy phenyl motif, and
   b) acetylation reaction: acetylating said product to obtain the Apremilast.

2. The method according to claim 1, wherein the asymmetric reagent is an asymmetric metal reagent.

3. The method according to claim 2, wherein the asymmetric metal reagent is formed with a metal reagent and an asymmetric ligand.

4. The method according to claim 3, wherein the asymmetric metal reagent is a metal Rh(I)-catalyst.

5. The method according to claim 4, wherein the reaction environment comprises a solvent.

6. The method according to claim 5, wherein the solvent is an alcoholic solvent.

7. The method according to claim 6, wherein the solvent is methanol.

8. The method according to claim 4, wherein the reaction environment comprises an additive.

9. The method according to claim 8, wherein the additive is a basic reagent.

10. The method according to claim 9, wherein the basic reagent is triethylamine.

11. The method according to claim 3, wherein the metal reagent and the asymmetric ligand can be in catalytic amounts.

12. The method according to claim 11, wherein the catalytic amount of the metal reagent is 5 mol %, and the addition amount of the asymmetric ligand is 6 mol %.

13. The method according to claim 5, wherein the specific temperature is from 0 to 150° C.

14. The method according to claim 13, wherein the specific temperature is about 60° C.

15. The method according to claim 14, wherein the β-phthalimino vinylsulfone is

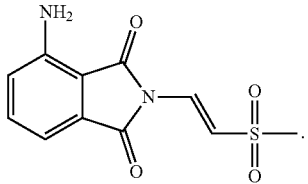 [SMILES: CS(=O)(=O)/C=C/N1C(=O)c2cccc(N)c2C1=O]

16. The method according to claim 3, wherein the asymmetric ligand is an asymmetric diene.

17. The method according to claim 16, wherein the asymmetric diene is

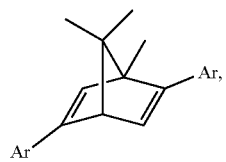

wherein Ar is selected from one of the following groups: phenyl ($C_6H_5$), 4-methylphenyl (4-Me-$C_6H_4$), 2-naphthyl, 1-naphthyl, biphenylyl (Ph-$C_6H_4$) tert-butylphenyl (t-Bu-$C_6H_4$), 4-fluorophenyl (4-F—$C_6H_4$), 4-chlorophenyl (4-Cl—$C_6H_4$) and 4-nitrophenyl (4-$NO_2$—$C_6H_4$).

18. The method according to claim 17, wherein Ar of the asymmetric diene is a phenyl group.

19. The method according to claim 10, wherein the nucleophile is a boronic acid.

20. The method according to claim 19, wherein the boronic acid is

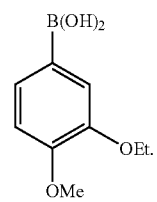 [SMILES: CCOc1cc(B(O)O)ccc1OC]

21. The method according to claim 19, wherein the equivalent ratio of the β-phthalimino vinylsulfone, the boronic acid and the triethylamine is 1:3:1.

22. The method according to claim 19, wherein the asymmetric ligand is

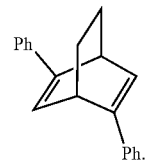

23. The method according to claim 22, wherein the equivalent ratio of the β-phthalimino vinylsulfone, the boronic acid and the triethylamine is 1:2:1.

24. The method according to claim 23, wherein the product is

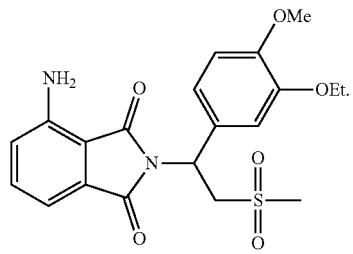 [SMILES: CCOc1cc(C(CS(C)(=O)=O)N2C(=O)c3cccc(N)c3C2=O)ccc1OC]

25. The method according to claim 24, wherein the product is S-form.

26. The method according to claim 25, wherein the acetylation reaction is to stir a mixture of the product and an acetic anhydride ($Ac_2O$) at 70° C. for three hours.

* * * * *